(12) United States Patent
Manderson

(10) Patent No.: US 7,141,052 B2
(45) Date of Patent: Nov. 28, 2006

(54) SURGICAL INTRAMEDULLARY IMPLANT WITH IMPROVED LOCKING FOR FIXATION OF FRACTURED BONE SEGMENTS

(75) Inventor: Easton L. Manderson, 800 Tucker Rd., Ashton, MD (US) 20861

(73) Assignee: Easton L. Manderson, Ashton, MD (US)

( * ) Notice: Subject to any disclaimer, the term of this patent is extended or adjusted under 35 U.S.C. 154(b) by 245 days.

(21) Appl. No.: 10/706,922

(22) Filed: Nov. 14, 2003

(65) Prior Publication Data

US 2005/0107792 A1    May 19, 2005

(51) Int. Cl.
 *A61B 17/58* (2006.01)
(52) U.S. Cl. ..................................... 606/62
(58) Field of Classification Search ............... 606/62, 606/63, 64, 79, 80, 85, 86, 95, 99
 See application file for complete search history.

(56) References Cited

U.S. PATENT DOCUMENTS

| | | | |
|---|---|---|---|
| 4,733,654 A * | 3/1988 | Marino | 606/64 |
| 5,993,456 A * | 11/1999 | Speitling et al. | 606/98 |
| 6,932,818 B1 * | 8/2005 | Behrens | 606/64 |
| 2003/0097131 A1* | 5/2003 | Schon et al. | 606/62 |
| 2005/0101958 A1* | 5/2005 | Adam | 606/64 |

* cited by examiner

*Primary Examiner*—Eduardo C. Robert
*Assistant Examiner*—James L. Swiger
(74) *Attorney, Agent, or Firm*—Antonelli, Terry, Stout & Kraus, LLP

(57) ABSTRACT

To set a fractured bone using an intramedullary nail having a hole for a proximal locking screw, the surgeon reams a primary cavity extending from a proximal area, across a fractured area, and into a distal area of the fractured bone, to a first diameter. An expanded cavity is also reamed in the proximal area of the fractured bone. The reamed primary and expanded cavities are aligned. The intramedullary nail is inserted so as to extend from the expanded cavity to a distal end of the primary cavity. With the intramedullary nail inserted, a bone fragment in the proximal area of the fractured bone, which covers the hole, is removed. The proximal locking screw is inserted through the uncovered hole and into the proximal area of the fractured bone without the use of a jig. The removed bone fragment is then secured back onto to the proximal area of the fractured bone from which it was removed, after insertion of the screw.

7 Claims, 18 Drawing Sheets

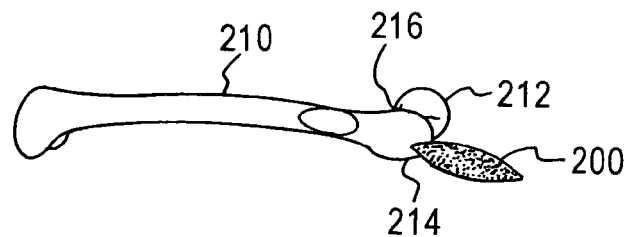
FIGURE 2A
(PRIOR ART)
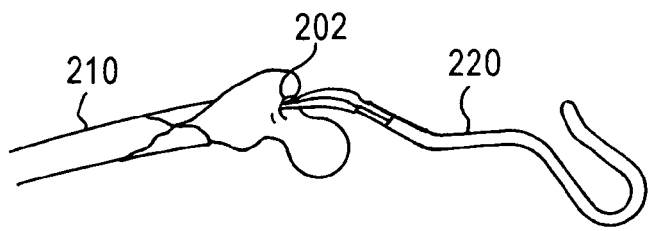
FIGURE 2B
(PRIOR ART)
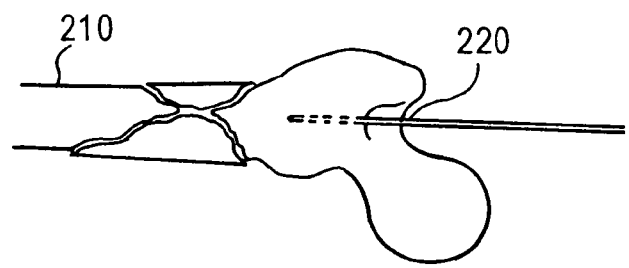
FIGURE 2B'
(PRIOR ART)
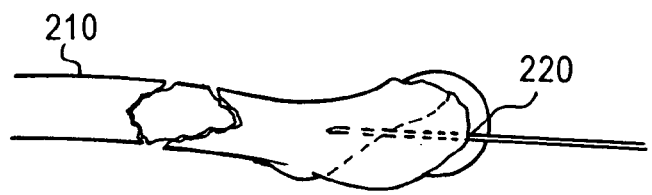
FIGURE 2B"

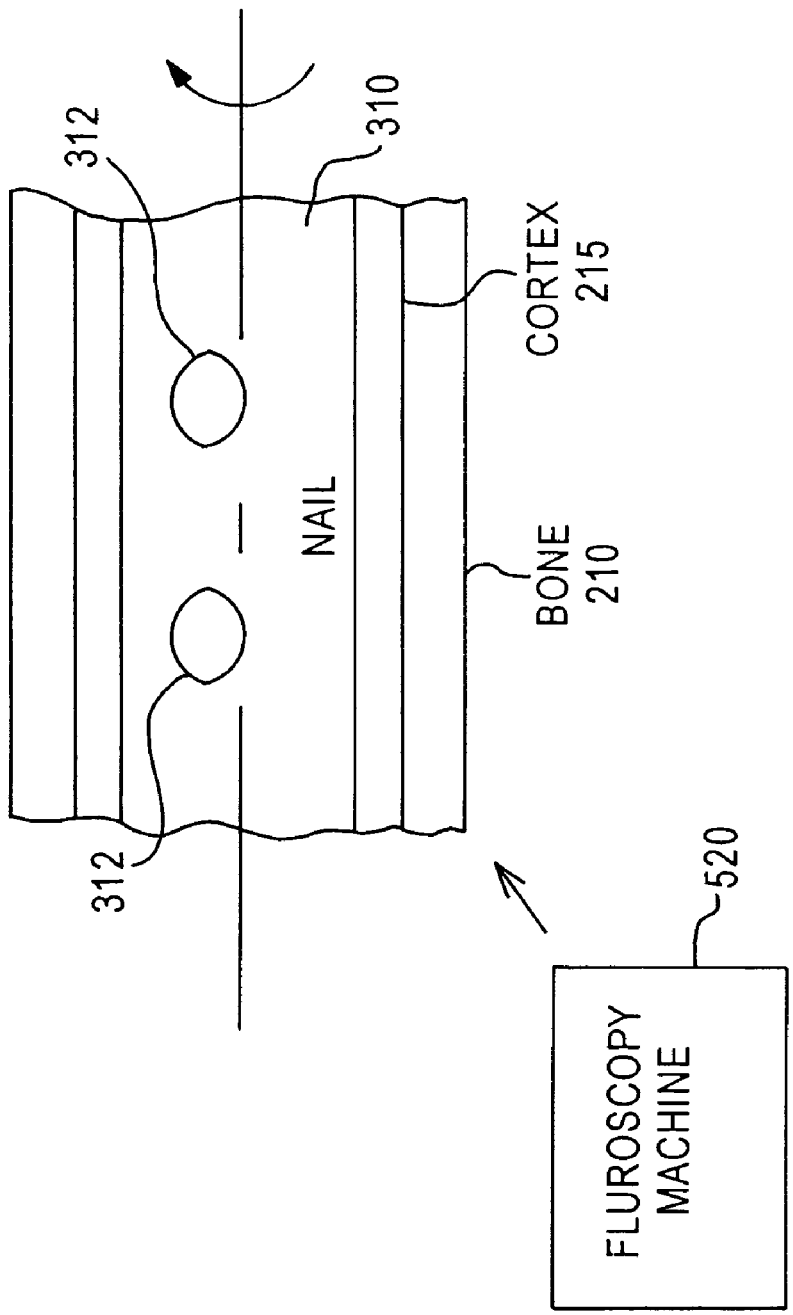

SURGICAL INTRAMEDULLARY IMPLANT WITH IMPROVED LOCKING FOR FIXATION OF FRACTURED BONE SEGMENTS

TECHNICAL FIELD

The present invention relates to surgical intramedullary implants for setting bone fractures, and more particularly to a surgical intramedullary implant with improved locking for fixation of fractured bone segments.

BACKGROUND OF THE INVENTION

The conventional method of intramedullary nailing of a fractured or broken femur, as shown in FIG. 1A, requires first placing the patient 100 on the fracture table 110 for the surgical treatment e.g., intramedullary nailing of a left femur. The patient is shown to be in a supine position, that is, lying on his/her back. The feet are placed in a traction device 120 which holds the femur stretched out to length. In the majority of cases, this will be sufficient to allow the surgical procedure to proceed. FIG. 1B shows a frontal projection of the patient 100 in the supine position.

The position of the broken fragments is monitored by an x-ray machine called a "fluoroscopy machine" (not shown) which provides real-time x-ray images to the surgeon. It will be recognized that some surgeons would prefer that the patient be placed on the side with the injured extremity extending upwards. FIG. 1C shows a posterior projection of a patient 100 placed in the lateral position, with the patient 100 on his/her side. FIG. 1D shows a frontal projection of the patient 100 on the fracture table 110 in the lateral position, with the fractured side upwards.

Referring to FIGS. 2A–2F, after the location of the incision in the applicable thigh and femur is prepared by cleansing and sterilizing, an incision 200 is made over the proximal end 212 of the femur 210 in the area that will be referred to as the "greater trochanter" 214. FIG. 2A depicts an incision 200, with the normal dissection performed on the area of the trochanter 214 and the neck 216 of the femur 210, which is the broken bone in the present example. Proper retraction is made with the tracking table 110 and the startable area is identified. This is just medial to the greater trochanter 214 described above.

A starter hole 202 can be made using either of two procedures. An awl 220, as shown in FIG. 2B, or a guide wire with a sharp end (not shown) is used to make the starter hole. FIGS. 2B' and 2B'' depict different views of the awl 220 as it makes the starter hole.

Once the starter hole is made, reaming using reamer 230 is begun. Reaming is usually performed over a guide wire. In some cases, if the traction described earlier does not place the broken fragments in the proper alignment and reduction, a procedure can be performed, after partial reaming from the proximal end 212, across the fracture 219, to the distal end 218 of the main proximal fragment, to insert a short internal fracture alignment device (not shown) or short intermedular rod (not shown) to improve the alignment reduction. The reaming at different stages is shown in FIGS. 2C and 2D.

Once the fracture is sufficiently reduced and aligned, with proper length restoration attained to the satisfaction of the surgeon, a guide wire 240 with a ball tip 242 is inserted with a hammer (not shown). The guide wire 240 is pushed down through the intermedular area to the distal end 218 of the femur 210. That is, the guide wire 240 is pushed into the distal fragment. Usually the guide wire 240 will stop at a desired area, such as the old epiphyseal line or just proximal to the kneecap in the present example. The positions of the guide wire 240 are monitored using the fluoroscopy machine as described above. FIG. 2E depicts the termination of the ball tip guide wire 240. It will be noted that the guide wire 240 has calibrations 244 to show how deep the wire has been inserted. This enables the surgeon to choose the appropriate length of the nail. Alternatively, as shown in FIG. 2E, the determination of nail length can be made by using a metal ruler 246 strapped to the skin. With the ruler 246, the necessary depth and the necessary length of the nail are determined using the fluoroscopy machine.

FIG. 2F depicts the reaming process over an already implanted ball tipped guide wire 240. The reaming with the reamer 230 proceeds up to the desired diameter of the nail. For each individual patient there are limitations on the reamed diameter due to the constraints of the cortical surfaces. The determination of precisely how much reaming to do is made by the surgeon on a case-by-case basis.

Referring now to the images in FIGS. 3A and 3B, after the reaming of the intermedullary cavity of both fragments, i.e. the bone on both sides of the fracture 219, the proximal fragment 212 which broke and the distal fragment 218 of the femur 210 remain aligned and traversed by a ball tipped guide wire 240. A plastic sleeve (not shown) is inserted into the reamed cavity over the ball tipped guide wire 240. This allows removal of the guide wire 240 while still maintaining the alignment and reduction attained in the previous steps. Another guide wire 300 is inserted through the plastic sleeve. This latter guide wire 300 does not have a ball tip at the end, and is therefore easily removable after insertion of a nail into the reamed cavity.

FIG. 3A depicts the initial insertion of the nail 310 into the reamed cavity. FIG. 3B shows the nail 310 being inserted with an attached handle 322 and jig 320 to allow hammering of the nail 310 to its proper depth with a hammer or slaphammer (as shown). Attached to the jig 320 in FIG. 3B is an angle guide 324. After the nail 310 is seated, the angle guide 324 is used to prepare the nail for a locking screw or screws.

Referring now to FIGS. 4A and 4B, the jig 320 is shown in place, with the hammer or slaphammer removed. As shown in FIG. 4A, a drill 400 is aligned by the jig 320 to be at a predetermined angle in order to ensure that the drill bit 402 will be directed through the predrilled holes in the nail 310 and will exit at the lesser trochanter 213, which is the smaller prominence on the opposite side of the bone from the greater trochanter 214. As shown in FIG. 4B, after drilling, a depth gauge 410 is used to select the proper length of the locking screw. At this point it should be noted that in some fractures of the femur 210, the surgeon may decide that the locking screw should go essentially from the greater trochanter area 214 through the predrilled hole in the nail 310, and be fixed firmly into the lesser trochanter 213. On the other hand, the surgeon may decide that, because of the fracture, a different type jig (not shown) will be used to allow insertion of a screw or screws into the femoral neck 216 and head of the femur 210. The choice is made by the surgeon on a case-by-case basis.

It should also be noted that, in many cases, it is considered necessary to secure the reduction obtained by the traction described above, both proximal and distal locking screws are necessary. Using a jig 500, such as that shown in FIGS. 5A and 5A', to secure distal locking of the nail 310, which typically has two holes in its distal portion, has not been very successful in practice. Variations in position of a millimeter or more can make it very difficult to insert distal locking screws.

This is because the surgeon must place the screws through an incision similar to the proximal incision described above, up through cortical bone, and into the predrilled holes in the metal intermedullary nail 310. A misalignment of a millimeter or so will make it impossible to advance the screws through the near cortex and both cortices of the nail 310, and to be secured in a far cortex. Therefore, in practice, distal locking jigs 500 have generally been abandoned because of the great difficulty experienced in successfully in placing distal locking screws using a jig technique.

Instead, the freehand technique is commonly used by surgeons today. The freehand technique requires a sharp tipped awl 500 or a sharp tipped guide wire (not shown). A fluoroscopy machine 520 is also used in this technique. Using this technique, the surgeon must place his/her hand in the field of radiation emitted by the fluoroscopy, i.e. x-ray, machine. In accordance with this technique, the fluoroscopy machine 520 is moved so that the distal holes 312 in the nail 310 perfect circles in the fluoroscopy image, as shown in FIG. 5C. Once these perfect circles are obtained, the distal end of the awl 510 or the sharp tipped rigid guide wire is aligned perfectly with this round hole. This must be done twice, since it is generally recommended that at least two distal locking screws of appropriate size be placed to fix the distal portion of the nail 310 to the femur 210. This is very difficult to do and exposes the surgeon, who may be required to perform the freehand technique a number of times each month or year, to dangerous levels of radiation.

FIG. 5B depicts the maneuvering required in the freehand technique to try to place the tip of the awl 510 in the perfectly circular holes. Once the surgeon considers the awl 510 to be properly positioned, a starting hole is made by the awl to start the hole in the near cortex 215 of the femur 210. After this is completed, and the image of the hole remains a perfect circle, i.e. the hole 312 stays where it is supposed to be according to the fluoroscopy machine 520, a power drill is used to make the hole through the near cortex, so as to be perfectly aligned with the hole 312 in the nail 310. The drilled hole extends from the near side of the nail 310 to the far side of the nail, and then finally into the far side of the cortex. If this is successful, a depth gauge is used to determine the proper screw length and then the screw is placed, as the drill was, across the near cortex of the femur 210, the near cortex of the nail, the far cortex of the nail 310 and the far cortex of the femur.

Needless to say, the fluoroscopy machine 520 has to stay positioned throughout the procedure, because even after drilling it can be difficult to find the weight bearing drilled nail hole 312. As noted above, this procedure must be repeated to allow placement of two or more screws. The femur 210 will take four to eight months to heal, before weight bearing is allowed. In the vast majority of the cases, if only one distal screw is used it will break, making the bone more susceptible to infection and making removal of the screw fragments almost impossible.

FIGS. 5C and 5C' demonstrate the use of the fluoroscopy machine 520 to show the difference in the profile of the predrilled holes 312 in the distal nail 310. A non-circular hole is shown in FIG. 5C' and a perfectly circular hole is shown in FIG. 5C.

OBJECTIVES OF THE INVENTION

It is an objective of the present invention to simplify the fixation of fractured bone segments.

Additional objects, advantages, novel features of the present invention will become apparent to those skilled in the art from this disclosure, including the following detailed description, as well as by practice of the invention. While the invention is described below with reference to preferred embodiment(s), it should be understood that the invention is not limited thereto. Those of ordinary skill in the art having access to the teachings herein will recognize additional implementations, modifications, and embodiments, as well as other fields of use, which are within the scope of the invention as disclosed and claimed herein and with respect to which the invention could be of significant utility.

SUMMARY DISCLOSURE OF THE INVENTION

The present invention provides and improved method for use by a surgeon in setting a fractured bone, e.g. a femur. The method utilizes an intramedullary nail having a first, preferably threaded, hole for a proximal locking screw. It should be understood that the locking screw could be any type of suitable fastener. In accordance with the invention, a primary cavity extending from a proximal area, across a fractured area, and into a distal area of the fractured bone, is reamed to a first diameter. An expanded cavity in the proximal area of the fractured bone is also reamed. Typically, the expanded cavity is reamed after the reaming of the primary cavity, although this is not mandatory. The primary and expanded cavities are reamed so as to be in alignment.

The intramedullary nail is inserted into the cavities by the surgeon. When fully inserted, the nail extends from the expanded cavity to the distal end of the primary cavity. With the intramedullary nail inserted, a bone fragment covering the first hole is removed from the proximal area of the fractured bone. The removal of this bone fragment makes the first hole visible to the naked eye of the surgeon, and therefore facilitates the insertion of the proximal locking screw, as will be discussed further below.

The proximal locking screw is inserted through the first hole and into the proximal area of the fractured bone without using a jig. That is, the surgeon inserts the proximal locking screw freehand, and without the aid of any type of alignment device. If the fractured bone is a femur, the proximal locking screw can be inserted into either the greater trochanter or the lesser trochanter. After insertion of the proximal locking screw, the removed bone fragment is secured back onto the proximal area of the fractured bone, from which it was removed.

Beneficially, the nail also has a second, preferably threaded, hole for a distal locking screw. If so, a hole is drilled in the distal area of the fractured bone to expose the second hole in the intramedullary nail. The distal locking screw is inserted through the second hole and into the distal area of the fractured bone. The insertion of the distal locking screw is also performed without the aid of a jig or other type alignment device. Advantageously, the locking screws have hollow cores. If so, a solid filler screw is inserted into the hollow core of each screw by the surgeon.

In accordance with other aspects of the invention, the surgeon can select a first nail member having the first hole for the proximal locking screw, and a second nail member having the second hole for the distal locking screw. This selection is generally based on attributes of the fractured bone. The surgeon then attaches the selected first and second nail members together to form the intramedullary nail.

BRIEF DESCRIPTION OF DRAWINGS

FIG. 2A depicts an incision being made at the proximal end of a fractured femur.

FIG. 2B depicts a starter hole being made in the fractured femur using an awl.

FIG. 2B' is a further depiction of the awl of FIG. 2B forming the starter hole.

FIG. 2B" depicts a different view of the formation of the starter hole as shown in FIG. 2B'.

FIG. 2E' depicts a non-calibrated ball tipped guide wire inserted into the reamed cavity of the femur with a measuring device to determine the length of the nail.

FIG. 5A' depicts another view of the jig of FIG. 5A.

FIG. 5C' depicts the imaging of the same holes shown in FIG. 5C with the nail at a slightly different rotational orientation.

FIG. 6E' depicts an alternative torquing groove in the head of the screw shown in FIG. 6D.

FIG. 7D' depicts an alternative torquing groove in the head of the screw shown in FIG. 7C.

BEST MODE FOR CARRYING OUT THE INVENTION

Figure 1A:
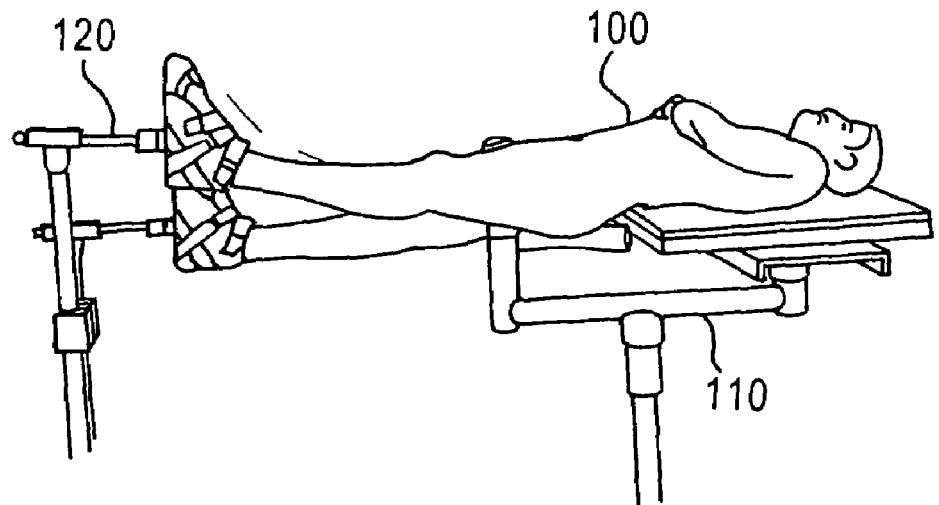
FIG. 1A depicts a side view of a conventional fracture table and traction device.
Figure 1B:
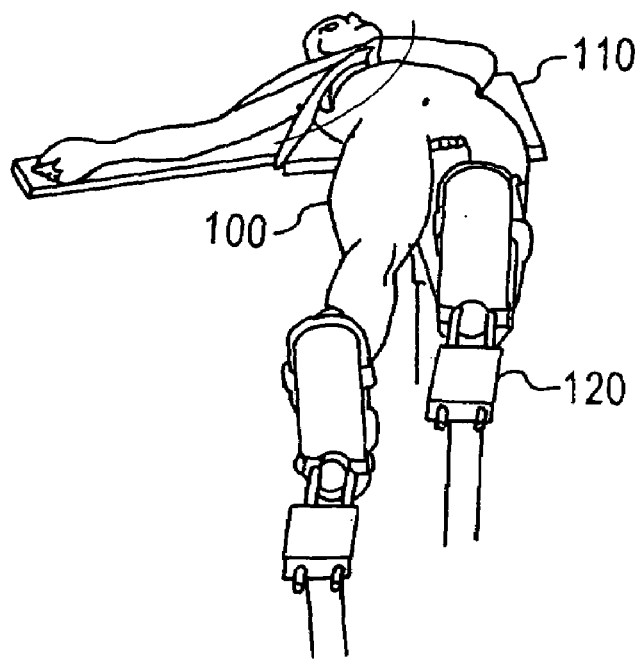
FIG. 1B depicts a frontal view of the fracture table and traction device of FIG. 1A.
Figure 1C:
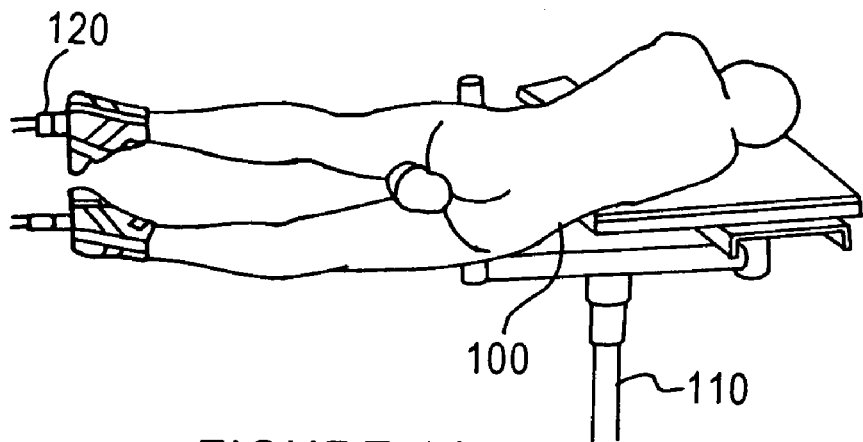
FIG. 1C depicts another side view of the fracture table and traction device of FIG. 1A.
Figure 1D:
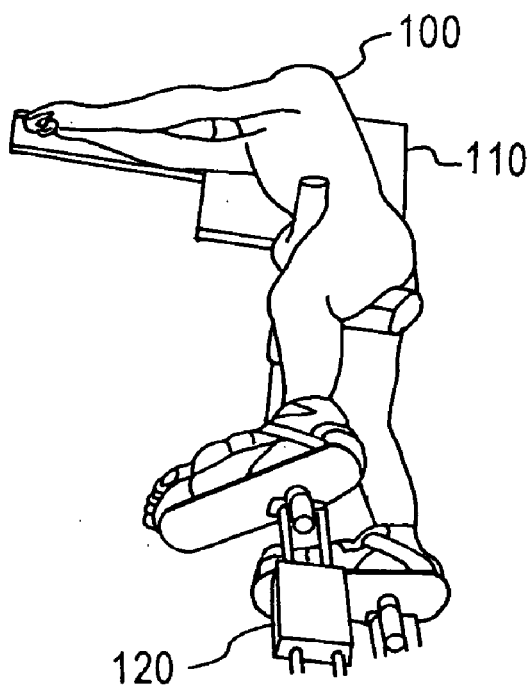
FIG. 1D presents another frontal view of the fracture table and traction device of FIG. 1A.
Figure 2C:
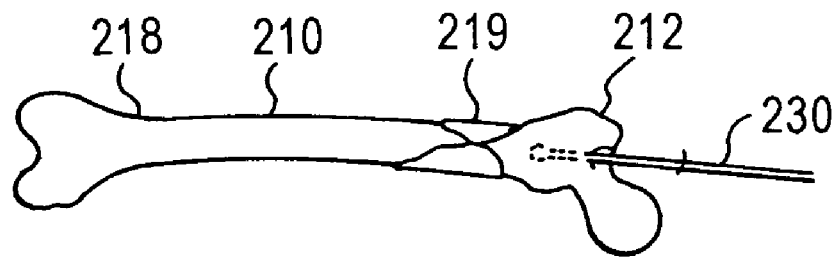
FIG. 2C depicts the reaming from the proximal end of the femur using a reamer.
Figure 2D:
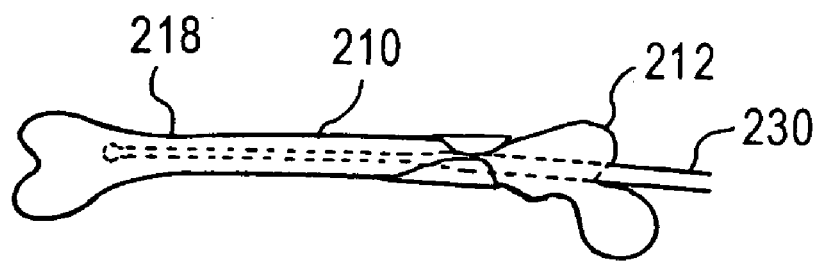
FIG. 2D depicts the reamer of FIG. 2C fully extended to the end of the reamed cavity in the femur.
Figure 2E:
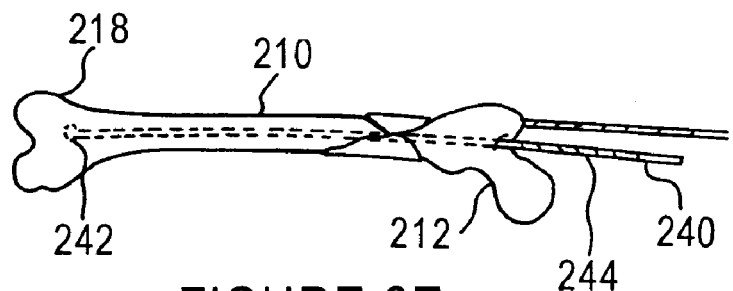
FIG. 2E depicts the insertion of a ball tipped guide wire within the reamed cavity of the femur.
Figure 2E:
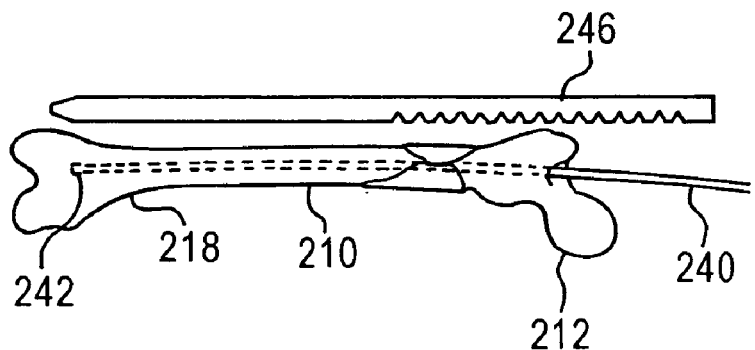
Figure 2F:
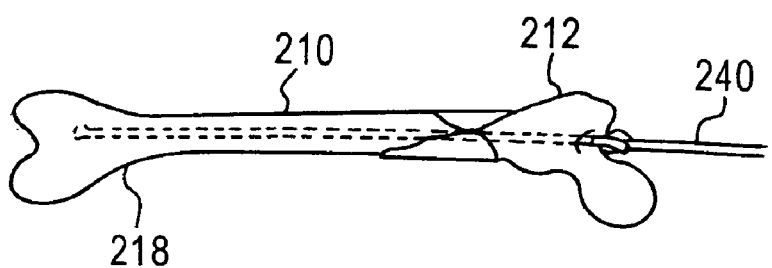
FIG. 2F depicts the ball tipped guide wire positioned to allow further reaming to the desired diameter of the nail.
Figure 3A:
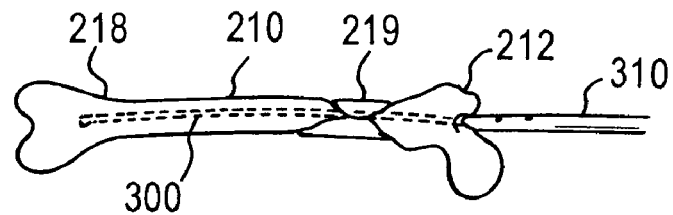
FIG. 3A depicts the beginning of the insertion of the nail into the reamed cavity.
Figure 3B:
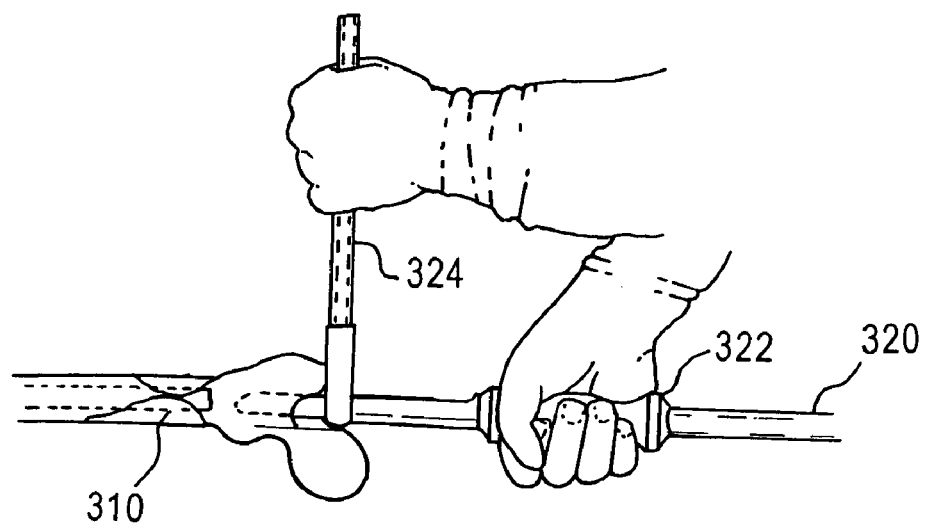
FIG. 3B depicts the use of a jig and hammer to insert the nail into the reamed cavity.
Figure 4A:
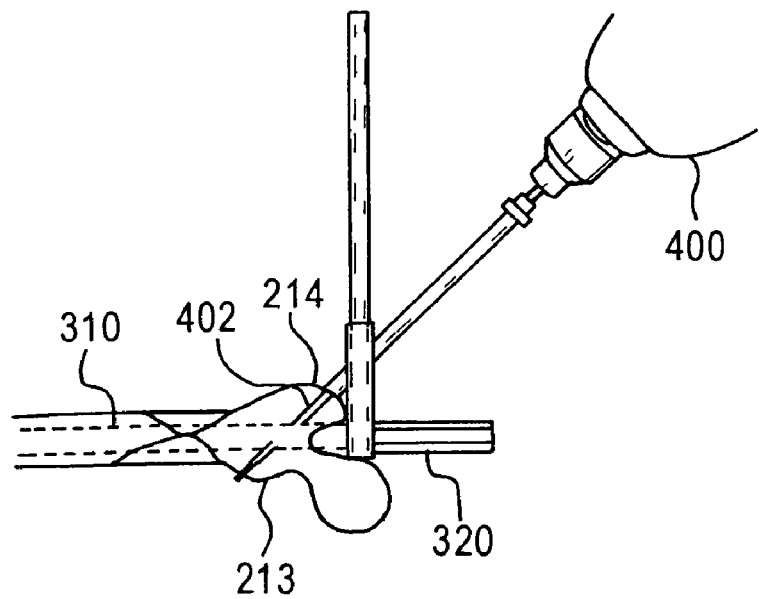
FIG. 4A depicts the conventional drilling of the femur for insertion of the locking screws using the jig depicted in FIG. 3B.
Figure 4B:
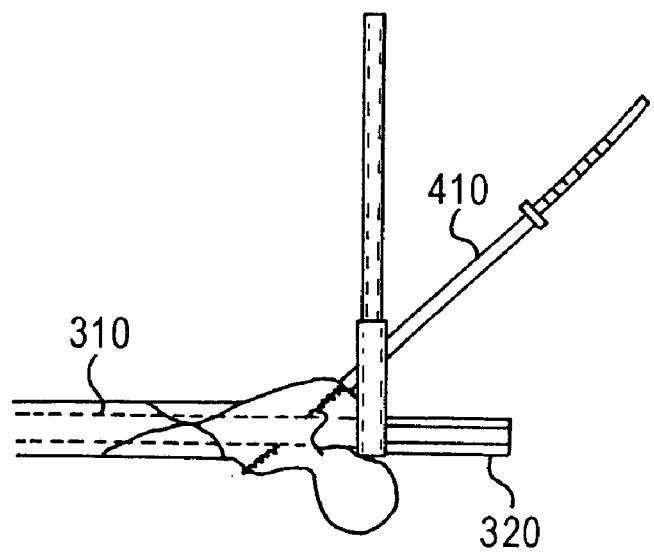
FIG. 4B depicts the measuring of the drilled hole for selection of the proper screw length using a depth gauge.
Figure 5A:
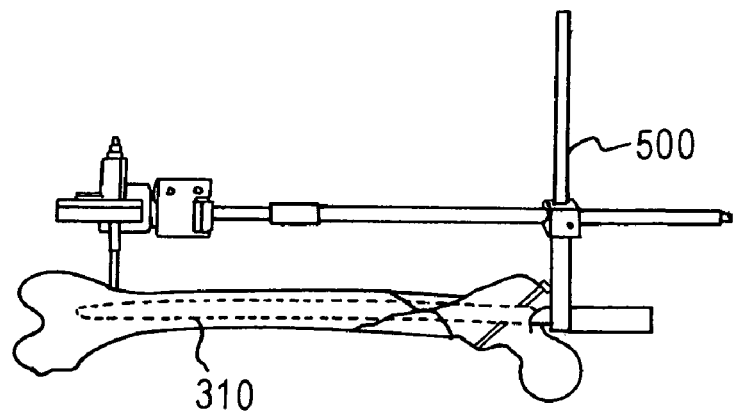
FIG. 5A depicts a jig conventionally utilized to set distal locking screws in a femur.
Figure 5A:
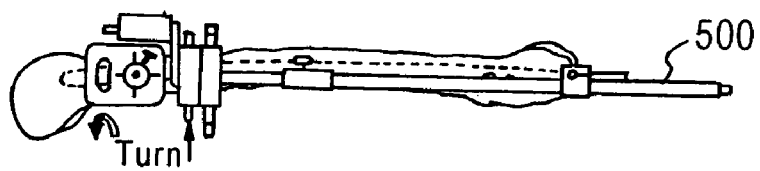
Figure 5B:
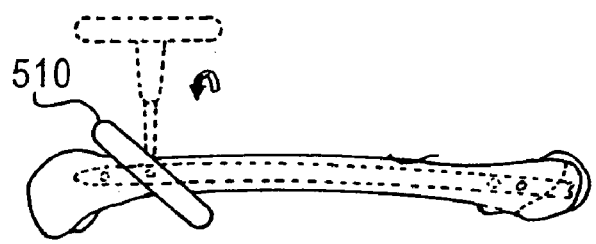
FIG. 5B depicts convention freehand setting of distal locking screws in a femur using an awl.
Figure 5C:
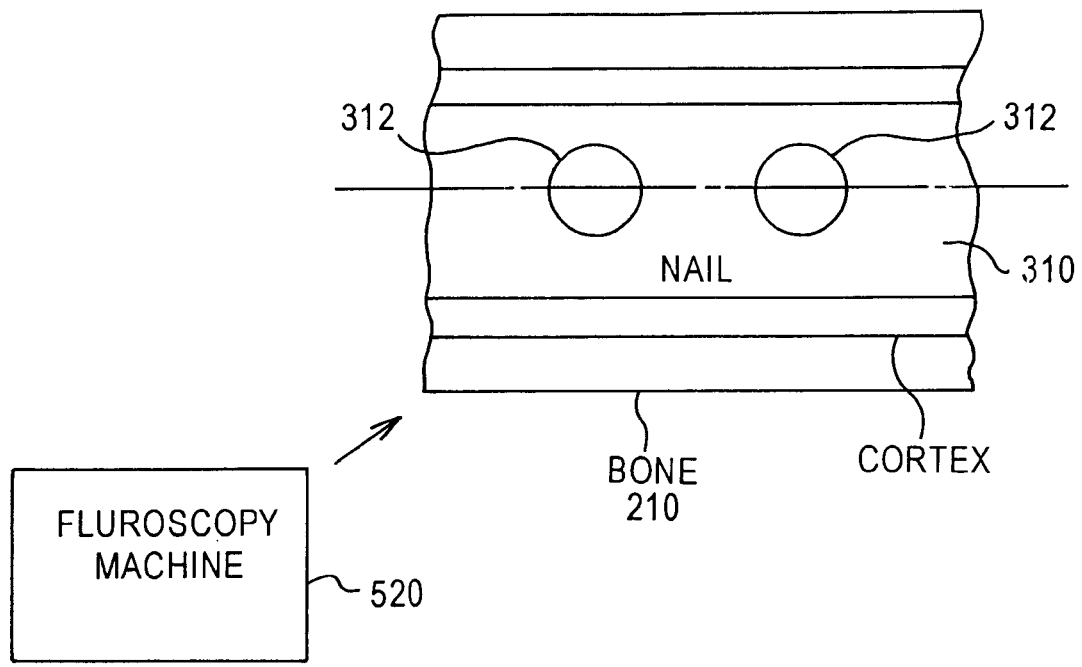
FIG. 5C depicts the imaging of the screw holes and a nail in a first rotational orientation.
Figure 6A:
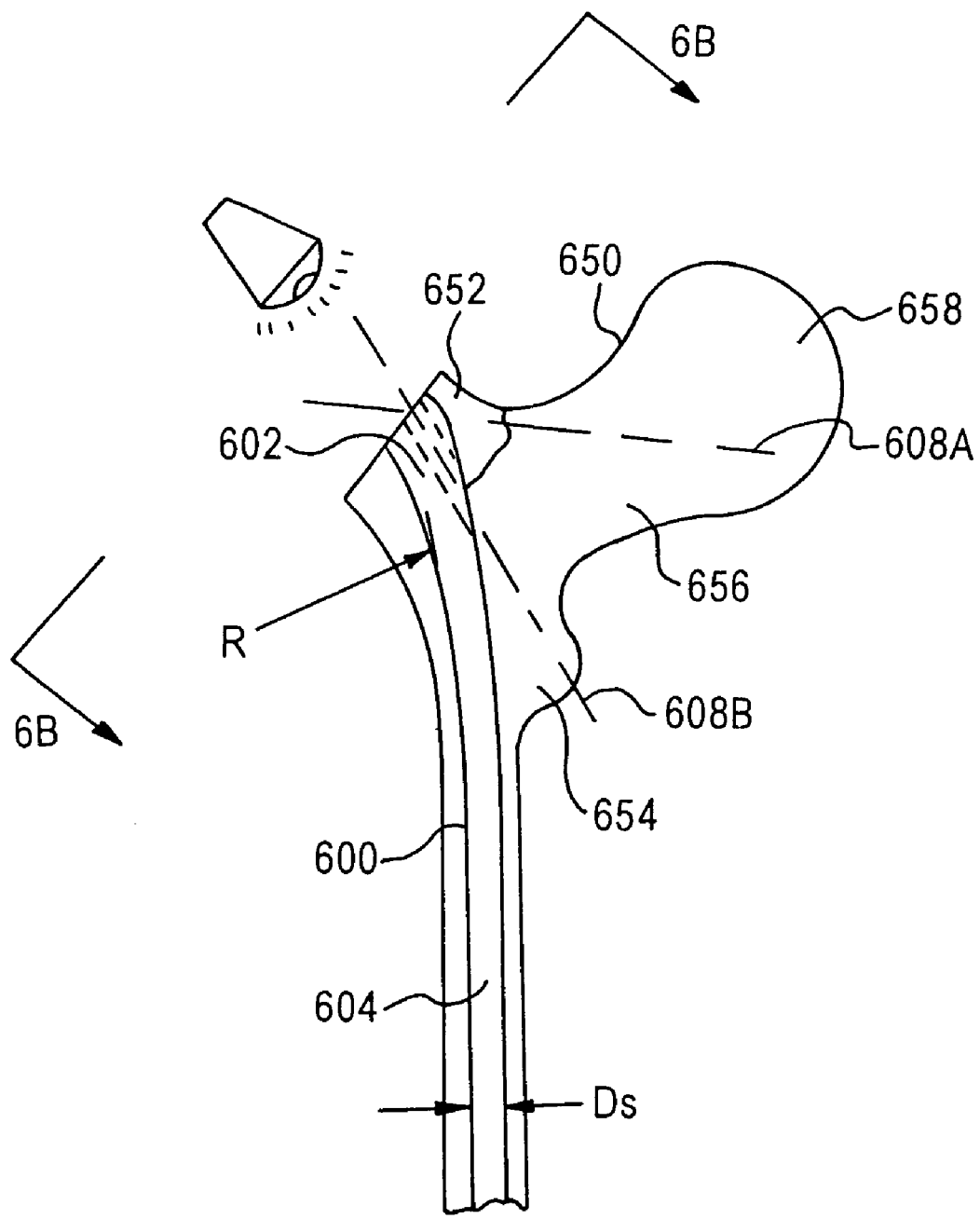
FIG. 6A depicts a nail inserted in a fractured femur in accordance with the present invention.
Figure 6B:
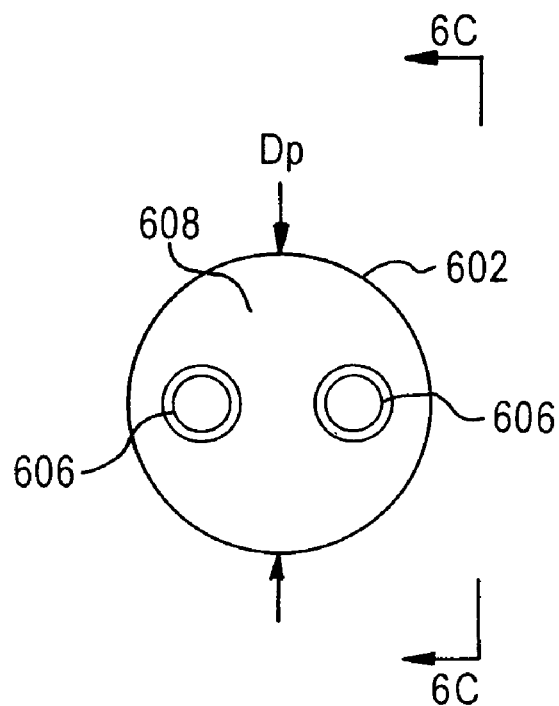
FIG. 6B depicts a proximal end view of the nail shown in FIG. 6A.
Figure 6C:
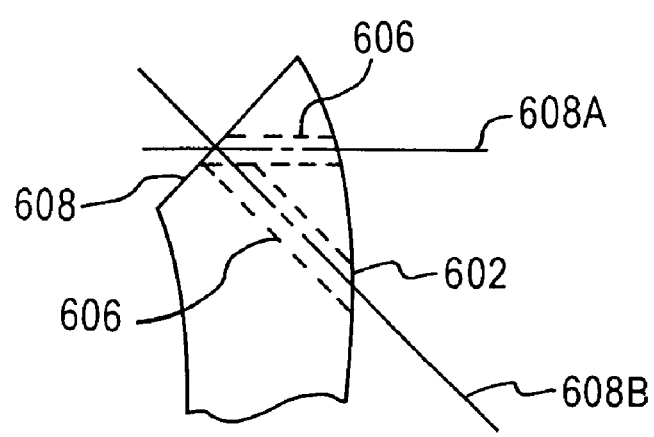
FIG. 6C depicts a side view of the proximal end of the nail depicted in FIG. 6A.
Figure 6E:
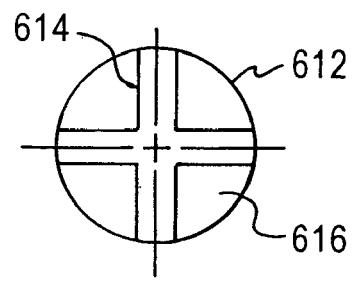
FIG. 6E depicts torquing grooves in the head of the screw shown in FIG. 6D.
Figure 6D:
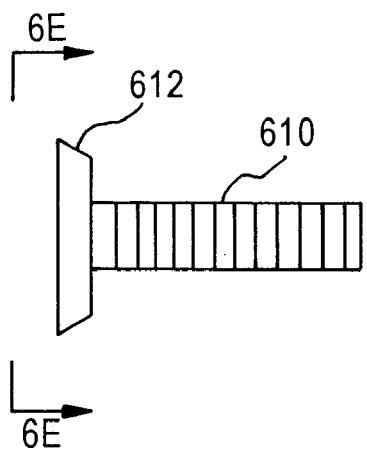
FIG. 6D depicts a screw suitable for use in locking the proximal end of the nail shown in FIG. 6A.
Figure 6E:
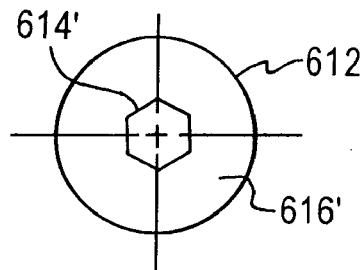

In accordance with the invention, and except as otherwise described below, the preparation of the patient and the surgical incision are performed as described previously. A starting hole, as in conventional techniques, will be made in the greater trochanter, and a guide wire will be inserted through the greater trochanter, and into the intermedullary canal, stopping at the predetermined end of the distal femur. Once the wire has been seated properly, as confirmed by a fluoroscopy machine, reaming of the proximal end of the femur in the trochanter area will be performed with different size reamers. The proximal end of the greater trochanter can be reamed up to 17 millimeters. This size will vary depending upon the individual patient. That is, the reaming will be customized to accommodate the varied anatomy of individual patients.

Referring now to FIGS. 6A–6E', the nail 600 has a proximal end 602, with a diameter Dp which is larger by 2, 3 or 4 millimeters, or even more, than the diameter of the shaft portion 604 of the nail. The proximal end 602 will have a maximum diameter of 17 millimeters corresponding to the maximum diameter of the reamed hole. The diameter Ds of the shaft portion 604 of the nail 600 is in the range of 9–14 mms, and is selected by the surgeon based on the size of the intermedullary canal, as is well understood in the art.

After reaming is performed to accommodate the larger proximal end 602 of nail 600, the nail 600 is seated over a guide wire as previously described. More particularly, both a reaming and a non-ball tipped guide wire for placement of the nail, are utilized.

Once the nail 600 is seated, a fragment portion 652 of the greater trochanter 650 of the femur will be removed, without disturbing the attachments, to allow direct visualization of pre-drilled holes 606 in the proximal end 602 of the nail 600. These holes 606 are angled in the face 608 of the proximal end 602 of the nail 600. Because of the orientation of these holes, a guide wire can be used to determine whether the subsequently inserted attachment screws will exit from the nail 600 into the bone of the lesser trochanter 654 along centerline 608B or, if desired, the neck 656 and be seated in the subcapped area in the head 658 of the femur along centerline 608A.

The guide wires are necessary to ensure that the orientation, e.g. rotation, of the nail 600 is proper, so that the attachment screws will not exit the outer surface of neck 656 of the femur or the cortical outer surface of the lesser trochanter 654. This can be confirmed with anterior, posterior, lateral and even oblique images generated by a fluoroscopy machine.

Once the proper orientation of the nail 600 has been confirmed, the guide wire is removed. The pre-drilled holes 606 in the proximal end 602 of the nail 600 will now guide either hollow or solid screws into the lesser trochanter 654 or head 658 of the femur to complete the locking of the nail 600 at its proximal end 602 to the femur.

Upon completion of the seating of the nail 600, the trochanter fragment 652 can be resutured to the greater trochanter. This will ensure that the bone fragment 652 will reattached itself to the femur in time.

The screws 610 have capped heads 612 to prevent entry of scar tissue or healing bone into the holes 606. One or more grooves 614 or 614' are provided in the face 616 or 616' of the head 612 for a screwdriver, Allen wrench or other type torquing device.

It should be recognized that the pre-drilled holes 606 could, if desired, be provided to allow the screws to be seated in the lesser trochanter area 654 or the subcapped portion of the head 658, or both. In such case, the surgeon can decide to insert the screw along either centerline 608A or 608B on a case-by-case basis.

Because the proximal end of the femur is larger and much wider than the distal end, the proximal end 602 of the nail 600 is much wider than the distal end of the nail. Therefore, the proximal end 602 is able to accommodate one or more screws for seating in the subcapped area of the head 658 or into the lesser trochantor 654.

Figure 7A:
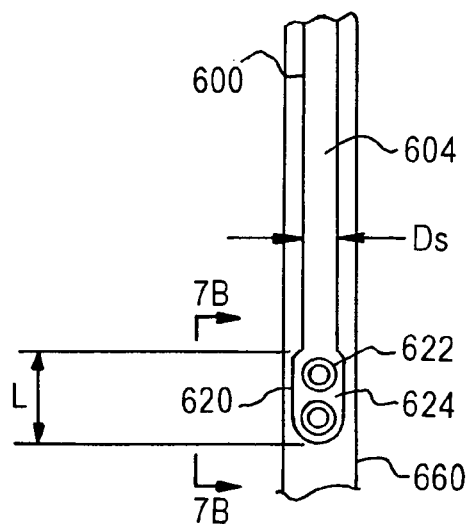
FIG. 7A depicts the distal end of the nail shown in FIG. 6A.
Figure 7B:
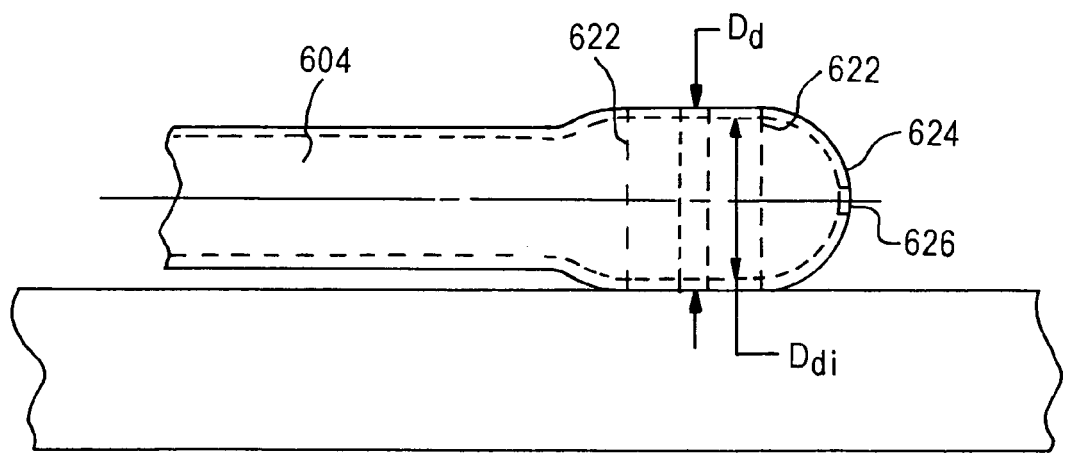
FIG. 7B depicts a side view of the distal end of the nail as shown in FIG. 7A.
Figure 7C:
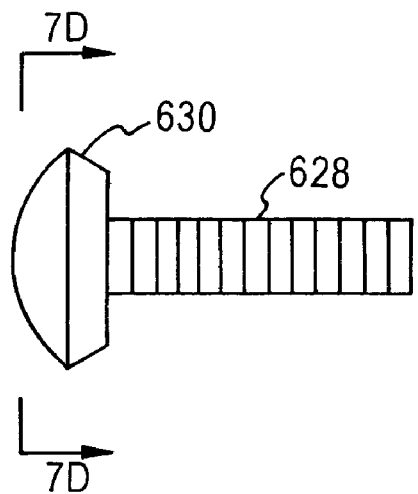
FIG. 7C depicts a screw suitable for use in locking the distal end of the nail shown in FIG. 7A.

Referring now to FIGS. 7A and 7B, unlike conventional nails, the locking hole or holes 622, in the distal end 620 of the nail 600 are at the very end of the nail. This allows a widened portion 624 at the end 620 of the nail 600 to accommodate variable size holes 622. The hole size is varied based on the length L of the expanding distal end portion 624 of the nail 600.

For example, with an 11 mm nail, the distal end portion 220 can be wider by 1–2 millimeters than the shaft 604. Thus, the distal end portion 620 will have a widened portion 624 with a diameter Dd of 12–13 millimeters. If a 12 mm diameter nail is used, the expanded distal end portion 624, which accommodates the distal locking hole or holes 622, may be 13 millimeters or even up to 14 millimeters in diameter. The reaming to accommodate the widened distal end portion 624 will be performed by using a 13–16 mm diameter reamer. As is customary, a reamer is typically selected so as to form a nail hole, which is 1–2 millimeters larger than the nail diameter. Accordingly, in the case of the 11 mm nail, the distal portion 660 of the fractured femur could be reamed up to 13 mm, thereby providing a 2 mm increase in the reamed diameter to accommodate the 11 mm diameter nail shaft 604 and distal end portion 624 of the nail 600. For a 12 mm diameter nail, the expanded distal end portion 624 could be 13 mm or 14 mm in diameter. Reaming to 14 mm will accommodate the 13 mm, and most probably even the 14 mm diameter of the expanded distal end portion 624 of the nail 600. It should be noted however, that, regardless of the reamed diameter, if difficulty is encountered in inserting the nail, it is likely that the expanded distal end portion 624 is the cause of the difficulty. In such a case, the nail should be removed and further reaming should be performed up to another millimeter. Hence, if a 12 mm nail with a 14 mm diameter expanded distal end portion 624 is difficult to seat, then the reaming should proceed up to 15 mm. The additional 1 mm in the reamed diameter will not create a problem because the nail 600 locked proximally and distally with the screws. Therefore, with the enlarged reamed diameter the nail 600 can be easily seated and will firmly hold the fragments of the fractured femur in good position.

FIG. 7B illustrates that the inner diameter Ddi of the cortices, so to speak, of the distal end 620 are preferably the same as the outer diameter Ds of the cortices of the shaft 604 of the nail 600. The distal end portion 620 of the nail 600 will have an aperture 626 or alternatively will be cannulated throughout to the far distal end, to accommodate an intermedullary guide wire. The distal locking screws 628 may be cortical held screws, having a head diameter to match the diameter of the distal hole or holes 622. The screws 628 engage both the near cortex and the far cortex of the distal portion of the femur. This engagement ensures firm fixation.

Once again, it is reemphasized that, at the distal end of the nail 600, the size of the holes 622 will be greater than the diameter of holes found in conventional nails. The increase in the diameter will be by an amount either exactly or substantially equal to the difference between the diameter Ds of the shaft 604 of the nail 600 and the diameter Dd of the expanded distal end portion 624, typically 2 millimeters. Furthermore, the diameter of the distal end 620 of the nail 600 will be a millimeter or more larger than that of a conventional nail.

The screws 628 are seated in the conventional manner. If necessary, a guide wire is inserted across the cortices from the near cortex and through the hole 622 of the distal end 620, engaging the far cortex of the femur. It is advisable, although not absolutely necessary, that the distal end 620 of the nail 600 accept at least two screws 628. Cannulated screws may be used to shorten the operative time, since such screws can be placed over the guide wires, and are therefore typically much easier to engage in the holes. Needless to say, a cannulated drill bit would also be needed, if a guide wire is used to insert cannulated screws. The use of cannulated or solid screws will provide sufficient structural strength to prevent rotational or other malalignment.

Figure 7D:
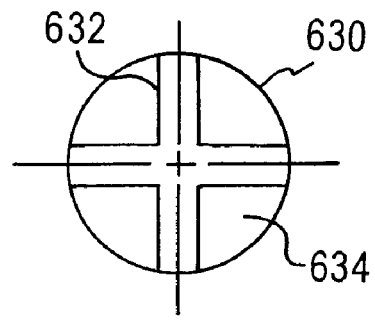
FIG. 7D depicts a torquing groove in the head of the screw shown in FIG. 7C.
Figure 7D:
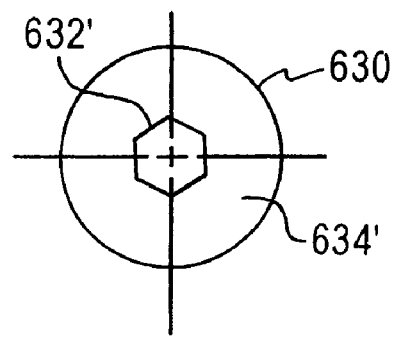

The screws 628 have capped heads 630 to prevent entry of scar tissue or healing bone into the holes 622. As described above, the outer surface of the head is curved to match the curvature of the outer surface of the expanded distal end portion 624. As shown in FIGS. 7D and 7D', one or more grooves 632 or 632' are provided in the face 634 or 634' of the head 630 for a screw driver, Allen wrench or other torquing device.

Figure 8A:
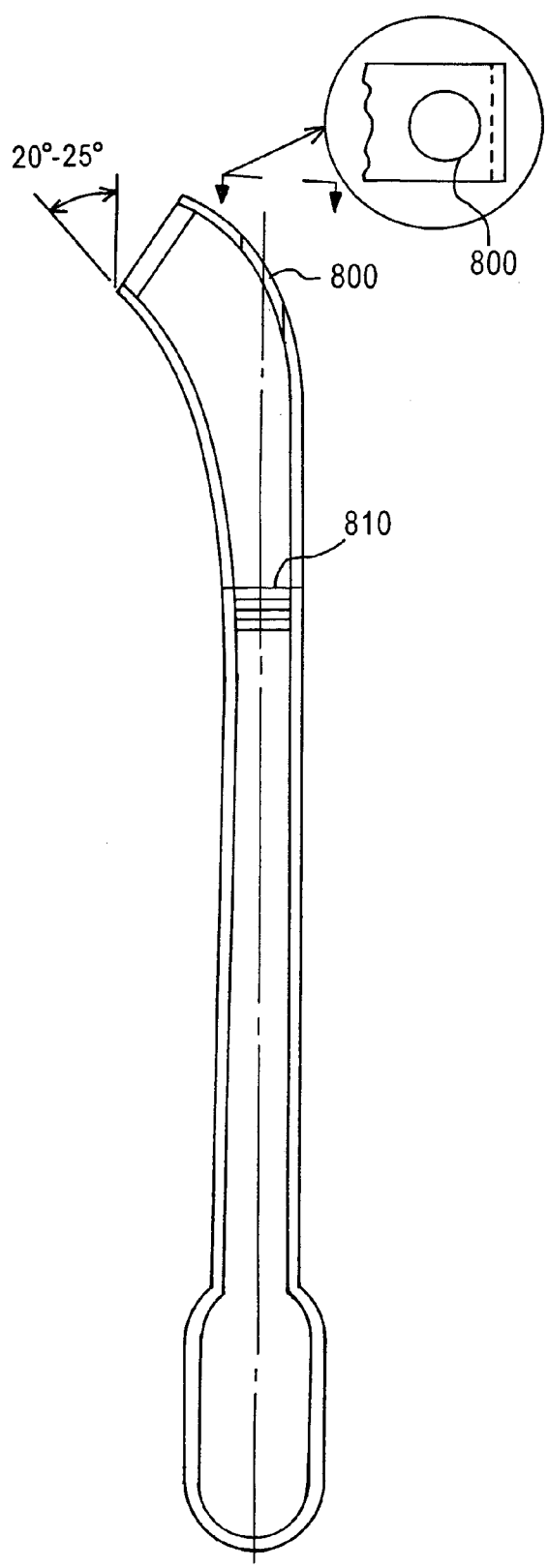
FIG. 8A depicts a cross-section of the nail shown in FIGS. 6A and 7A.

FIG. 8A depicts a cross-section of the nail described above with reference to FIGS. 6A and 7A. As shown, the proximal end of the nail is preferably curved approximately an angle of 20° to 30° off vertical. The nail also includes an aperture 800 in an upper portion of the proximal end of the nail directly above a threaded portion 810 formed along the inner diameter of the proximal end portion of the nail. A driver for use in implanting or extracting the nail is inserted through the aperture and torqued until locked by the threads 810. Thus, the aperture 800 and threads 810 will provide a positive lock between the nail and the driver to facilitate insertion of the nail into the reamed cavity and removal of the inserted nail from the reamed cavity by the surgeon. It will also be recognized that, if desired, an extraction awl can be utilized for removal. In such a case, the tip of the awl will be inserted through the aperture 800 but will not be locked by the threads 810. Rather, the hook at the end of the awl can be moved so as to bear against an inner surface of the nail as it is pulled by the surgeon to thereby extract the nail from the reamed cavity.

Figure 8B:
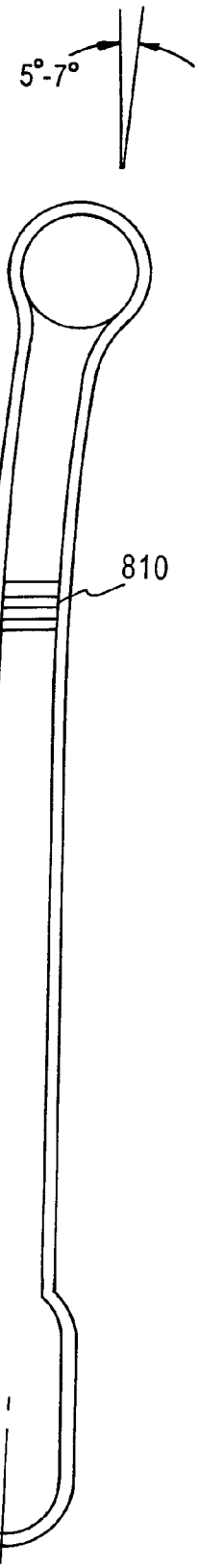
FIG. 8B depicts a different cross-section of the nail shown in FIG. 8A.

FIG. 8B depicts another cross-section of the nail shown in FIG. 8A. As shown, the nail has secondary curvature of the proximal end. This curvature angles the proximal end in the range of 5° to 7°.

Figure 9A:
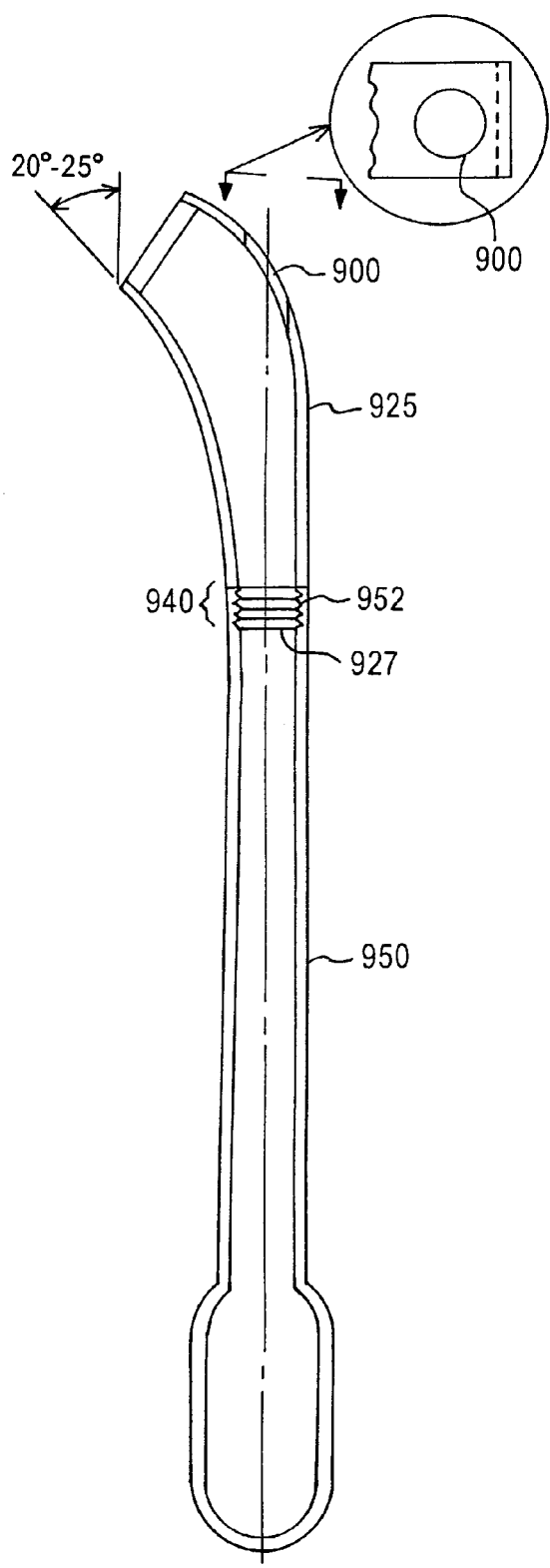
FIG. 9A depicts a cross-section of a nail similar to that shown in FIG. 8A formed of two separate members.
Figure 9B:
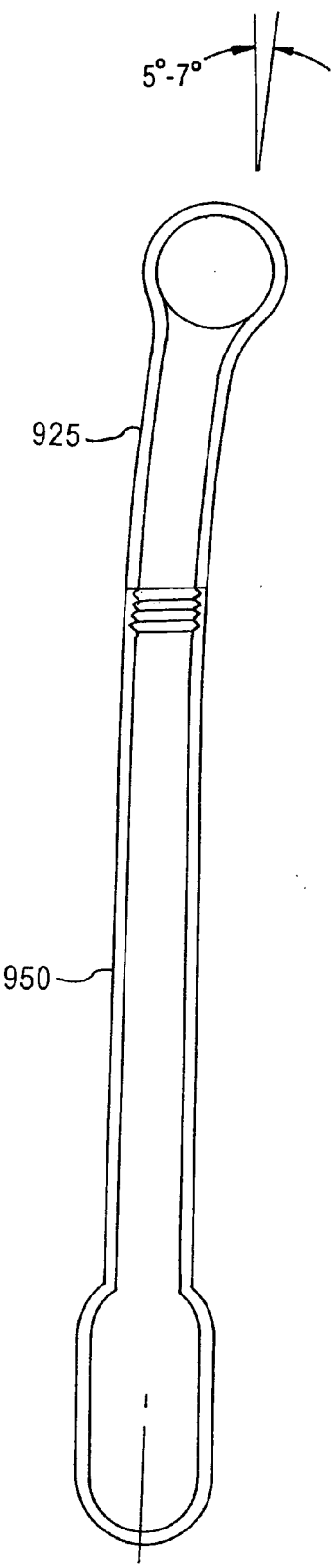
FIG. 9B depicts a different cross-section of the nail shown in FIG. 9A.

FIGS. 9A and 9B depict a cross-section of a nail similar to the nail shown in FIGS. 8A and 8B. However, the nail shown in FIGS. 9A and 9B is modular. More particularly, the nail is formed of two separate members, i.e. proximal end member 925 and distal end member 950. As shown, the proximal end member 925 and the distal end member 950 both include threaded portions in the area identified by reference numeral 940. In the case of proximal end member 925, the threaded portion 927 and area 940 includes treads on both the inner and outer diameter. The distal end portion 950 includes treads along its inner diameter in the area 940. The outer diameter treads 927 of the proximal end portion lock with the inner diameter treads 952 of the distal end portion to form the nail. A driver or extractor can then be inserted through the aperture 900 and torqued to lock to the inner diameter treads 927 of the proximal end portion 925 for installation and removal of the nail to or from the reamed cavity.

It should be noted that the modular configuration of the nail shown in FIGS. 9A and 9B allows a surgeon to utilize any desired number of proximal end portions with a relatively small number of distal end portions to create a wide variety of nails having different proximal end orientations and lengths. The modular configuration also allows manufacturers to provide the modular components to form a vast array of different nails while needing to only maintain an inventory of a relatively small number different distal end portions. Potentially, the manufacturer could even limit itself to only one type distal end portion which can be utilized with any number of proximal end portions to form the desired nail.

Figure 10:
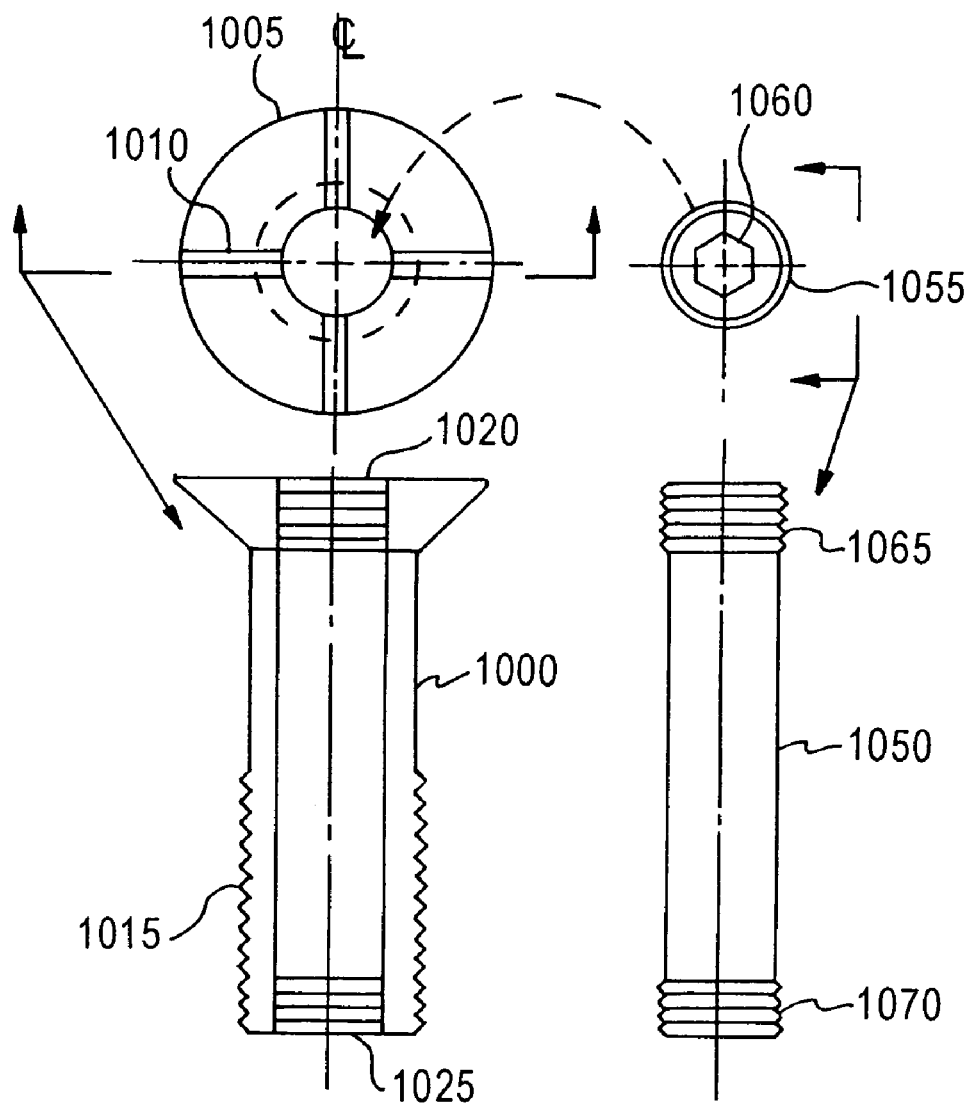
FIG. 10 depicts a locking screw for locking a nail.

FIG. 10 depicts a screw particularly suitable for use in locking both the proximal and distal ends of the previously described nails. The screw shown in FIG. 10 can also be beneficially utilized to lock conventional nails.

The size of the locking screws will typically be selected by the surgeon. The selected screws may be fully or partially threaded. Preferably, the screws will be 5.0, 6.0, 7.3, 16.0, or 32.0 mm in diameter. Beneficially, cannulated partially or fully threaded screw will be utilized to lock the nail to the bone. The same size screws are generally recommended for locking both the proximal and distal ends of the nail.

If cannulated screws are utilized, the screws can be guided by a guide wire inserted into the drilled screw holes.

As shown in FIG. 10, beneficially a partially threaded cannulated screw 1000 is utilized to lock both the proximal and distal ends of the nail. A groove 1010 is provided in the head 1005 of the screw to torque the screw 1000 such that the threads 1015 on the outer diameter of the screw 1000 engage the inner diameter of the drilled hole to lock the nail in place.

The screw 1000 includes inner diameter threads 1020 and 1025 for engaging a solid metal insert 1050. As shown, the insert 1050 includes a groove 1060 in the insert head 1055 for torquing the insert 1050. The insert 1050 includes outer threads 1065 and 1070 which engage with the threads 1020 and 1025 of the screw 1000 as the insert is torqued via groove 1060. The screw 1000, with the solid metal insert 1050 provides additional strength against breakage, while still allowing the use of guide wires for installation of the screw into the nail locking position.

It will also be recognized by those skilled in the art that, while the invention has been described above in terms of one or more preferred embodiments, it is not limited thereto. Various features and aspects of the above described invention may be used individually or jointly. Further, although the invention has been described in the context of its implementation in a particular environment and for particular purposes, e.g. orthopedics, those skilled in the art will recognize that its usefulness is not limited thereto and that the present invention can be beneficially utilized in any number of environments and implementations. Accordingly, the claims set forth below should be construed in view of the full breath and spirit of the invention as disclosed herein.

What is claimed is:

1. A method of setting a fractured bone using an intramedullary nail having a first hole for a proximal locking screw and a second hole for a distal locking screw, comprising:
    reaming a primary cavity extending from a proximal area, across a fractured area, and into a distal area of the fractured bone, to a first diameter;
    reaming an expanded cavity in the proximal area of the fractured bone, wherein the primary and the expanded cavities are aligned;
    inserting the intramedullary nail so as to extend from the expanded cavity to a distal end of the primary cavity;
    removing a bone fragment from the proximal area of the fractured bone to expose the first hole in the inserted intramedullary nail;
    inserting the proximal locking screw through the exposed first hole and into the proximal area of the fractured bone without use of a jig; and
    securing the removed bone fragment to the proximal area of the fractured bone from which the bone fragment was removed, after insertion of the proximal locking screw.

2. The method according to claim 1, wherein:
    the fractured bone is a femur;
    the proximal area of the fractured bone includes at least one of a greater trochanter and a lesser trochanter of the femur; and
    the proximal locking screw is inserted into one of the greater trochanter and the lesser trochanter.

3. The method according to claim 1, wherein the proximal locking screw has a hollow core, and further comprising:
    inserting a solid filler screw into the hollow core of the inserted proximal locking screw.

4. The method according to claim 1, wherein:
    with the bone fragment removed from the proximal area of the fractured bone, the first hole is visible to the naked eye of the surgeon.

5. The method according to claim 1, further comprising:
    selecting a first nail member having the first hole for the proximal locking screw, and a second nail member having the second hole for the distal locking screw, based on attributes of the fractured bone; and
    attaching the selected first nail member to the selected second nail member to form the intramedullary nail.

6. The method according to claim 1, further comprising:
    drilling a hole in the distal area of the fractured bone to expose the second hole in the intramedullary nail; and
    inserting the distal locking screw through the exposed second hole and into the distal area of the fractured bone without use of a jig.

7. The method according to claim 6, wherein the distal locking screw has a hollow core, and further comprising:
    inserting a solid filler screw into the hollow core of the inserted distal locking screw.

* * * * *